United States Patent [19]
Hastings et al.

[11] Patent Number: 5,994,302
[45] Date of Patent: Nov. 30, 1999

[54] HUMAN VASCULAR IBP-LIKE GROWTH FACTOR

[75] Inventors: Greg A. Hastings, Germantown; Craig A. Rosen, Laytonsville, both of Md.

[73] Assignee: Human Genome Sciences, Inc., Rockville, Md.

[21] Appl. No.: 08/849,107

[22] PCT Filed: Dec. 9, 1994

[86] PCT No.: PCT/US94/14388

§ 371 Date: Sep. 25, 1997

§ 102(e) Date: Sep. 25, 1997

[87] PCT Pub. No.: WO96/17931

PCT Pub. Date: Jun. 13, 1996

[51] Int. Cl.$^6$ .................... A61K 38/18; C07K 14/475
[52] U.S. Cl. ................ 514/12; 530/399; 530/402
[58] Field of Search ................ 530/399; 514/2, 514/12

[56] References Cited

U.S. PATENT DOCUMENTS 5,019,559  5/1991  Antoniades ........................ 514/21

FOREIGN PATENT DOCUMENTS 8908667  9/1989  WIPO ..................... C07K 13/00
9000569  1/1990  WIPO ..................... C07K 15/12

OTHER PUBLICATIONS

Bradham, et al., "Connective Tissue Growth Factor; a Cysteine–rich Mitogen Secreted by Human Vascular Endothelial Cells Is Related to the SRC–induced Immediate Early Gene Product CEF–10", Journal of Cell Biology, vol. 114, No. 6, issued Sep. 1991, pp. 1289–1292.

M. Khorsandi et al. "Effects of Hypophysectomy on Vascular Insulin–Like Growth Factor–1 Gene Expression After Balloon Denudation in Rats", Atherosclerosis, vol. 93, issued 1992, pp. 115–122.

Dame, Genbank Locus T02533, 0146C3 Plasmodium falciparum cDNA; clone PF0146C, 1992.

Weissenbach, Genbank Locus HS274VE5, H. sapiens (D8S538) DNA segment containing (CA) repeat; clone AFM274ve5, 1994.

Bradham D. et al., J. Cell. Biol. 114:1285–1294 (1991).

Bar, R. et al., Endocrinology 125:1910–1920 (1989).

Yarden, Y. et al., Nature 323:226–232 (1986).

Ullrich, A. et al., The EMBO Journal 5:2503–2512 (1986).

Abboud, S. et al., J. Clin. Invest. 88:470–475 (1991).

Bork, P., FEBS 327:125–130 (1993).

Ryseck, R. et al., Cell Growth and Differentiation 2:225–233 (1991).

Igarashi, A. et al., Mol. Biol. Cell. 4:637–645 (1993).

Baxter, R. and Martin, J., Progress in Growth Factor Research 1:49–68 (1989).

O'Brien, T. and Lau, L., Cell Growth and Differentiation 3:645–654 (1992).

O'Brien, T. et al., Molecular and Cellular Biology 10:3569–3577 (1990).

Joliot, V. et al., Molecular and Cellular Biology 12:10–21 (1992).

Khorsandi, M. et al., Atherosclerosis 93:115–122 (1992).

*Primary Examiner*—John Ulm
*Assistant Examiner*—Christine Saoud
*Attorney, Agent, or Firm*—Michele M. Wales

[57] ABSTRACT

A human Vascular IBP-like growth factor polypeptide (VIGF) and DNA (RNA) encoding such polypeptide and a procedure for producing such polypeptide by recombinant techniques is disclosed. Also disclosed are methods for utilizing such polypeptide for wound healing or tissue regeneration, stimulating implant fixation and angiogenesis. Antagonists against such polypeptides and their use as a therapeutic to treat atherosclerosis, tumors and scarring are also disclosed. Diagnostic assays for identifying mutations in VIGF nucleic acid sequences and altered levels of the VIGF polypeptide are also disclosed.

22 Claims, 9 Drawing Sheets

```
                                                                           CTGCTTCCCACCAGCAAAGACCACGACTGGAGAGCCCGAGCAGCTGGGAAACATG
  1                                                                        ----------+---------+---------+---------+---------+---------+  60
                                                                           GACGAAGGGTGGTCGTTTCTGGTGCTGACCCTCTCGGCCTCGTCGACCCTTGTAC
                                                                                                                                       M

AAGAGCGTCTTGCTGCTGACCACGCTCCTCGTGCCTGCACACCTGGTGGCCGCTGGAGC
  61                                                                       ----------+---------+---------+---------+---------+---------+ 120
                                                                           TTCTCGCAGAACGACGACTGGTGCGAGGAGCACGGACGTGTGGACCACCGGCGACCTCG
                                                                            K  S  V  L  L  L  T  T  L  L  V  P  A  H  L  V  A  A  W  S

AATAATTATGCGGTGGACTGCCCTCAACACTGTGACAGCAGTGAGTGCAAAAGCAGCCCG
 121                                                                       ----------+---------+---------+---------+---------+---------+ 180
                                                                           TTATTAATACGCCACCTGACGGGAGTTGTGACACTGTCGTCACTCACGTTTCGTCGGGC
                                                                            N  N  Y  A  V  D  C  P  Q  H  C  D  S  S  E  C  K  S  S  P

CGCTGCAAGAGGACAGTGCTCGACGAGCTGCTCGACAGCTGTGCCGAGTGTGCCTGCAGGGCGG
 181                                                                       ----------+---------+---------+---------+---------+---------+ 240
                                                                           GCGACGTTCTCCTGTCACGAGCTGCTGACACCGACGAGCTCACACGGCGACGTCCCGCC
                                                                            R  C  K  R  T  V  L  D  D  C  G  C  C  R  V  C  A  A  G  R

MATCH WITH FIG. 1B       FIG.1A
```

MATCH WITH FIG. 1A

```
241  GGAGAAACTTGCTACCGCACAGTCTCAGGCATGATGGCATGAAGTGTGGCCCGGGCTG  300
     ----+----+----+----+----+----+----+----+----+----+----+----+
     CCTCTTTGAACGATGGCGTGTCAGAGTCCGTACTTCACGTACTTCACACCGGGCCCCGAC
      G  E  T  C  Y  R  T  V  S  G  M  D  G  M  K  C  G  P  G  L

301  AGGTGTCAGCCTTCTAATGGGGAGGATCCTTTTGGTGAAGAGTTTGGTATCTGCAAAGAC  360
     ----+----+----+----+----+----+----+----+----+----+----+----+
     TCCACAGTCGGAAGATTACCCCTCCTAGGAAAACCACTTCTCAAACCATAGACGTTTCTG
      R  C  Q  P  S  N  G  E  D  P  F  G  E  E  F  G  I  C  K  D

361  TGTCCCTACGGCACCTTCGGGATGGATTGCAGAGAGACCTGCAACTGCCAGTCAGGCATC  420
     ----+----+----+----+----+----+----+----+----+----+----+----+
     ACAGGGATGCCGTGGAAGCCCTACCTAACGTCTCTCTGGACGTTGACGTCAGTCCGTAG
      C  P  Y  G  T  F  G  M  D  C  R  E  T  C  N  C  Q  S  G  I

421  TGTGACAGGGGACGGGAAAATGCCTGAAATTCCCCTTCTTCCAATATTCAGTAACCAAG  480
     ----+----+----+----+----+----+----+----+----+----+----+----+
     ACACTGTCCCCCTGCCCTTTACGGACTTTAAGGGGAAGAAGGTTATAAGTCATTGGTTC
      C  D  R  G  T  G  K  C  L  K  F  P  F  F  Q  Y  S  V  T  K
```

MATCH WITH FIG. 1C

FIG. 1B

MATCH WITH FIG. 1B

481  TCTTCCAACAGATTTGTTCTCTCACGGAGCATGACATGGCATCTGGAGATGGCAATATT     540
     ----+----|----+----|----+----|----+----|----+----|----+----|
     AGAAGGTTGTCTAAACAAGAGAGTGCCTCGTACCGTAGACCTCTACGTTATAA
      S  S  N  R  F  V  S  L  T  E  H  D  M  A  S  G  D  G  N  I

541  GTGAGAGAAGAAGTTGTGAAAGAGAATGCTGCCGGGTCTCCCGTAATGAGGAAATGGTTA     600
     ----+----|----+----|----+----|----+----|----+----|----+----|
     CACTCTCTTCTTCAACACTTTCTCTTACGACGGCCCAGAGGGCATTACTCCTTTACCAAT
      V  R  E  E  V  V  K  E  N  A  A  G  S  P  V  M  R  K  W  L

601  AATCCACGCTGATCCCGGCTGTGATTTCTGAGAAGGCTCTATTTCGTGAYTGTTCAA       660
     ----+----|----+----|----+----|----+----|----+----|----+----|
     TTAGGTGCGACTAGGGCCGACACTAAAGACTCTCTTCCGAGATAAAGCACTRACAAGTT
      N  P  R  *

661  CACACAGCCAACATTTTAGGAACTTTCTAGATTATAGCATAAGGACATGTAATTTTTGAA    720
     ----+----|----+----|----+----|----+----|----+----|----+----|
     GTGTGTCGGTTGTAAAATCCTTGAAAGATCTAATATCGTATTCCTGTACATTAAAAACTT

721  GACCAAATGTGATGCATGGTGGATCCAGAAAACAAAAGTAGGATACTTACAATCCATAA    780
     ----+----|----+----|----+----|----+----|----+----|----+----|
     CTGGTTTACACTACGTACCACCTAGGTCTTTTGTTTTTCATCCTATGAATGTTAGGTATT

MATCH WITH FIG. 1D

FIG.1C

MATCH WITH FIG. 1C

```
781   CATCCATATGACTGAACACTTGTATGTGTTTGTTAAATATTCGAATGCATGTAGATTTGT
      ----+----+----+----+----+----+----+----+----+----+----+----+   840
      GTAGGTATACTGACTTGTGAACATACACAAACAATTTATAAGCTTACGTACATCTAAACA

841   TAAATGTGTGTGTATAGTAACACTGAAGAACTAAAAATGCAATTTAGGTAATCTTACATG
      ----+----+----+----+----+----+----+----+----+----+----+----+   900
      ATTTACACACACATATCATTGTGACTTCTTGATTTTTACGTTAAATCCATTAGAATGTAC

901   GAGACAGGTCAACCAAAGAGGAGCTAGGCAAGCTGAAGACCGCAGTGAGTCAAATTAG
      ----+----+----+----+----+----+----+----+----+----+----+----+   960
      CTCTGTCCAGTTGGTTTCTCCTCGATCCGTTCGACTTCTGGCGTCACTCAGTTTAATC

961   TTCTTTGACTTTGATGTACATTAATGTTGGGATATGGAATGAAGACTTAAGAGCAGGAGA
      ----+----+----+----+----+----+----+----+----+----+----+----+   1020
      AAGAAACTGAAACTACATGTAATTACAACCCTATACCTTACTTCTGAATTCTCGTCCTCT

1021  AGATGGGGAGGGGGTGGGAGTGGGAAATAAAATATTTAGCCCTTCCTTGGTAGGTAGCTT
      ----+----+----+----+----+----+----+----+----+----+----+----+   1080
      TCTACCCCTCCCCCACCCTCACCCTTTATTTTATAAATCGGGAAGGAACCATCCATCGAA
```

MATCH WITH FIG. 1E

FIG.1D

MATCH WITH FIG. 1D

```
1081  CTCTAGAATTTAATTRTGCTTTTTTTTTTTTTTGGGCTTTGGGAAAAGTCAAAATAAA  1140
      ----+----+----+----+----+----+----+----+----+----+----+----+
      GAGATCTTAAATTAAYACGAAAAAAAAAAAAACCCGAAACCCTTTCAGTTTTATTT

1141  ACAACCAGAAACCCCTGAAGGAAGTAAGATGTTTGAAGCTTATGGAAATTTGAGTAACA  1200
      ----+----+----+----+----+----+----+----+----+----+----+----+
      TGTTGGTCTTTTGGGACTTCCTTCATTCTACAAACTTCGAATACCTTTAAACTCATTGT

1201  AACAGCTTTGANCTGAGAGCAATTYCAAAAGGCTGCTGATCTAGCCCCCCGGGTTNCCTNT  1260
      ----+----+----+----+----+----+----+----+----+----+----+----+
      TTGTCGAAACTNGACTCTCGTTAARGTTTCCGACGACTACATCGGGGGCCCAANGGANA

1261  NTCTNAAGGAC  1271
      ----+----+-
      NAGANTTCCTG
```

FIG.1E

```
                1                                                           50
ce10_chick   ...MGSAGAR P.ALAAALLC LARLALGSPC PAV.....CQC ...PAA.APQ
cyr6_mouse   ...MSSSTFR TLAVAVTLAH LTRLAL.STC PAA.....CHC ...PLE.APK
ctgf_human   .MTAASMGPV RVAFVVLLAL CSRPAVGQNC SGP.....CRC ...PDEPAPR
fisp-12      .MLASVAGPI SLAL.VLLAL CTRTATGQDC SAQ.....CQC ...AAEAAPH
nov_chick    .METGGGQGL PVLLLLLLLL RPCEVSGREA ACPRPCGGRC ...PAEP.PR
ibp_3human   MQRARPTLWA AALTLLVLLR GPPVARAGAS SGGLGPVVRC EPCVARALAR
ccn-4        ........MK SVLLTTLLV PAHLVAAWSN MYAVDCPQHC DSSECKSSPR 51                                                           100
ce10_chick   CAPGVGLVP. .....DGCGCC KVCAKQLNED C.....SRTQP CDHTKGLECN
cyr6_mouse   CAPGVGLVR. .....DGCGCC KVCAKQLNED C.....SKTQP CDHTKGLECN
ctgf_human   CPAGVSLVL. .....DGCGCC RVCAKQLGEL C.....TERDP CDPHKGLFCD
ccn-4        ......... ........... ........... ........... ...........

401      411
ce10_chick   RLVNDIHKFR D
cyr6_mouse   SLFNDIHKFR D
ctgf_human   YYRKMYGDMA .
fisp-12      YYRKMYGDMA .
nov_chick    DPMSSEAKI. .
ibp3_human   .......... .
ccn-4        .......... .
```

FIG. 2

VICF/6-Histidine Fusion Protein Purification

LANE
1    Gibco BRL low range molecular weight standard
2    Pre-column Lysate
3    Column flow-through
4    pH 5.0 wash
5    pH 2.0 elvate

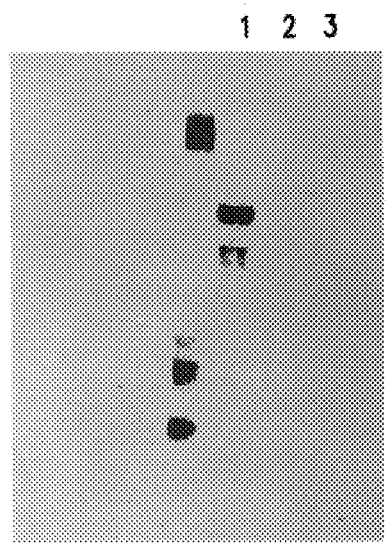
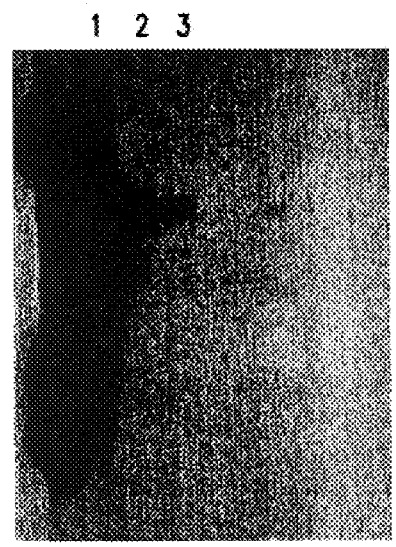
| Lane 1 | Umbilical Vein Endothelial Cells |
| Lane 2 | Aortic Smooth Muscle Cells |
| Lane 3 | Dermal Foreskin Fibroblast Cells |
FIG.5A
| Lane 1 | Umbilical Vein Endothelial Cells |
| Lane 2 | Aortic Smooth Muscle Cells |
| Lane 3 | Dermal Foreskin Fibroblast Cells |
FIG.5B

HUMAN VASCULAR IBP-LIKE GROWTH FACTOR

This application is a national stage application of PCT/US94/14388 filed Dec. 9, 1994, under 35 USC 371.

This invention relates to newly identified polynucleotides, polypeptides encoded by such polynucleotides, the use of such polynucleotides and polypeptides, as well as the production of such polynucleotides and polypeptides. The invention also relates to inhibiting the action of such polypeptides.

The polypeptide of the present invention is related to a family of growth regulators comprising cef 10/cyr 61, connective tissue growth factor (CTGF), and nov, as well as the insulin-like growth factor binding protein (IBP) family which modulates the activity of insulin-like growth factor (IGF). The mRNA corresponding to the polypeptide of this invention is highly expressed in vascular cell-types, thus, this polypeptide is hereinafter referred to as human vascular IBP-like growth factor or "VIGF".

Growth factors and other mitogens, including transforming oncogenes, are capable of rapidly inducing a complex set of genes to be expressed by certain cells (Lau, L. F. and Nathans, D., *Molecular Aspects of Cellular Regulation*, 6:165–202 (1991). These genes, which have been named immediate early or early response genes, are transcriptionally activated within minutes after contact with a growth factor or mitogen, independent of de novo protein synthesis. A group of these immediate early genes encodes secreted, extracellular proteins which are needed for coordination of complex biological processes such as differentiation and proliferation, regeneration and wound healing (Ryseck, R. P. et al, *Cell Growth Differ.*, 2:235–233 (1991).

Highly related proteins which belong to this group include cef 10 from chicken, which was detected after induction by the viral oncogene pp60$^{v-src}$ (Simmons, D. L. et al, *PNAS*, U.S.A., 86:1178–1182 (1989). A closely related protein, cyr 61, is rapidly activated by serum or platelet-derived growth factor (PDGF) (O'Brien, T. P. et al, *Mol. Cell Biol.*, 10:3569–3577 (1990). The overall amino acid identity between cef 10 and cyr 61 is as high as 83%. A third member is human connective tissue growth factor (CTGF) (Bradham, D. M. et al., *J. Cell. Biol.*, 114:1285–1294 (1991). CTGF is a cysteine-rich peptide which is secreted by human vascular endothelial cells in high levels after activation with transforming growth factor beta (TGF-β). CTGF exhibits PDGF-like biological and immunological activities and competes with PDGF for a particular cell surface receptor.

A fourth member of the immediate-early proteins is fisp-12, which has been shown to be induced by serum and has been mapped to a region of the murine genome (Ryseck, R. P. et al., *Cell Growth Differ.*, 2:235–233 (1991). Yet another member of this family is the chicken gene, nov, normally arrested in adult kidney cells, which was found to be overexpressed in myeloblastosis-associated virus type 1 induced nephroblastomas. Further, expression of an amino-terminal-truncated nov product in chicken embryo fibroblasts was sufficient to induce transformation (Joliot, V. et al., *Mol. Cell. Biol.*, 12:10–21 (1992).

The expression of these immediate early genes act as "third messengers" in the cascade of events triggered by growth factors. It is also thought that they are needed to integrate and coordinate complex biological processes, such as differentiation and wound healing in which cell proliferation is a common event.

This emerging family of growth regulators is called the CCN family for CTGF; cef 10/cyr 61; and nov. The VIGF polypeptide of the present invention is thought to be a member of this family of growth regulators. The VIGB polypeptide also contains a stretch of cysteines which is highly homologous to insulin-like growth factor (IGF)-binding protein.

At least two different binding proteins have been identified in adult human serum, namely, IGF-binding protein 53 and IGF-binding protein 1. The IGF-binding proteins have both stimulatory and inhibitory effects on IGF. Clemmons, et al, *J. Clin. Invest.*, 77:1548 (1986) showed increased binding to fibroblast and smooth muscle cell surface receptors of IGF in complex with its binding protein. The inhibitory effects of IGF-binding protein on various IGF actions in vitro, have been shown and they include stimulation of glucose transport by adipocytes, sulfate incorporation by chondrocytes and thymidine incorporation in fibroblast (Zapf, et al., *J. Clin. Invest.*, 63:1077 (1979)). In addition, inhibitory effects of IGF-binding proteins on growth factor mediated mitogen activity in normal cells has been shown.

In accordance with one aspect of the present invention, there is provided a novel mature polypeptide which is VIGF, as well as biologically active and diagnostically or therapeutically useful fragments, analogs and derivatives thereof.

In accordance with another aspect of the present invention, there are provided isolated nucleic acid molecules encoding human VIGF, including mRNAs, DNAs, cDNAs, genomic DNAs as well as analogs and biologically active and diagnostically or therapeutically useful fragments and derivatives thereof.

In accordance with yet a further aspect of the present invention, there is provided a process for producing such polypeptide by recombinant techniques comprising culturing recombinant prokaryotic and/or eukaryotic host cells, containing a human VIGF nucleic acid sequence, under conditions promoting expression of said protein and subsequent recovery of said protein.

In accordance with yet a further aspect of the present invention, there is provided a process of utilizing such polypeptide, or polynucleotide encoding such polypeptide for therapeutic purposes, for example, to treat muscle wasting diseases, osteoporosis, to aid in implant fixation, to stimulate wound healing or tissue regeneration, to promote angiogenesis and to proliferate vascular smooth muscle and endothelial cell production.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, to limit the production of excess connective tissue during wound healing or pulmonary fibrosis.

In accordance with yet a further aspect of the present invention, there are also provided nucleic acid probes comprising nucleic acid molecules of sufficient length to specifically hybridize to VIGF sequences.

In accordance with still another aspect of the present invention, there are provided diagnostic assays for detecting diseases related to the under-expression and over-expression of the VIGF polypeptide and mutations in the nucleic acid sequences encoding such polypeptide.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–1E shows the cDNA (SEQ ID NO:1) and corresponding deduced amino acid sequence (SEQ ID NO:2) of the VIGF polypeptide. The initial 21 amino acids represent the putative leader sequence such that the mature polypeptide comprises 163 amino acids. The standard one letter abbreviations for amino acids are used. Sequencing was performed using a 373 Automated DNA sequencer (Applied Biosystems, Inc.). Seqeuncing accuracy is predicted to be greater than 97% accurate.

FIG. 2 shows the amino acid sequence homology between VIGF and other proteins which are members of the CCN family. These members include: ce10__chick (SEQ ID NO:3); cyr6__mouse (SEQ ID NO:4); ctgf__human (SEQ ID NO:5); fisp__12 (SEQ ID NO:5); nov__chick (SEQ ID NO:7); and ibp__3human (SEQ ID NO:8).

FIGS. 5A–5B shows a gel which displays the results of a cell-type analysis of VIGF gene expression in the various tissues displayed. Lane 1 is umbilical vein endothelial cells, Lane 2 is aortic smooth muscle cells and Lane 3 is dermal foreskin fibroblast cells. FIG. 5A shows the results after a two hour exposure and FIG. 5B shows the results after a thirty-six hour exposure.

Figure 3:
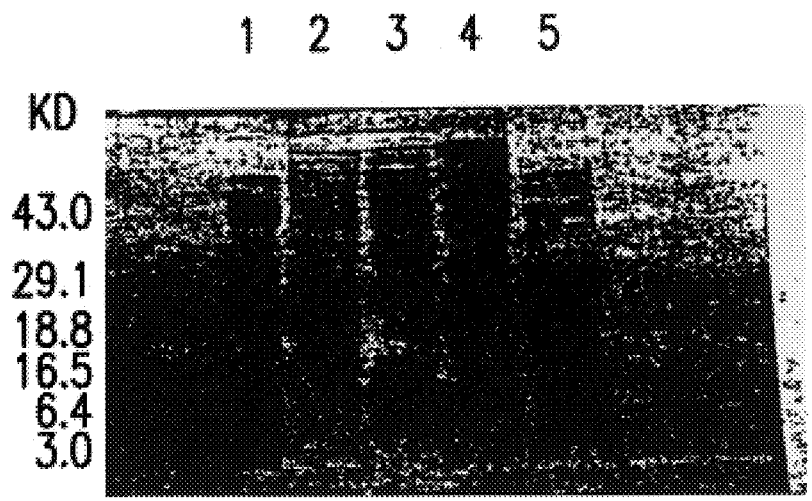
FIG. 3 shows an SDS-polyacrylamide gel which displays the results of VIGF bacterial purification and electrophoresis.

In accordance with an aspect of the present invention, there is provided an isolated nucleic acid (polynucleotide) which encodes for the mature polypeptide having the deduced amino acid sequence of FIGS. 1A–1E (SEQ ID NO:2) or for the mature polypeptide encoded by the cDNA of the clone deposited as ATCC Deposit No. 75874 on Aug. 25, 1994. The ATCC number referred to above is directed to a biological deposit with the ATCC, American Type Culture Collection, 10801 University Boulevard, Manassas, Va. 20110-2209. The strain is maintained under the terms of the Budapest Treaty and will be made available to a patent office signatory to the Budapest Treaty.

A polynucleotide encoding a polypeptide of the present invention may be obtained from human umbilical vein and aortic endothelial cells, aortic smooth muscle cells, and pulmonary artery. The polynucleotide of this invention was discovered in a cDNA library derived from human umbilical vein endothelial cells. It is structurally related to the IBP and CCN families. It contains an open reading frame encoding a protein of 184 amino acid residues of which approximately the first 21 amino acids residues are the putative leader sequence such that the mature protein comprises 163 amino acids.

The designation of VIGF as a hybrid member of both the CCN growth factor and IBP families was based primarily through conservation of amino acid sequences. Similarity of VIGF to the CCN family is inferred because of the 40–45% similarity over the entire polypeptide, 12 of a total of 18 VIGF cysteines are conserved, and 94% identity with the IBP signature (GCGCCXXCAXXXXXXC) (SEQ ID NO:9) which is perfectly conserved in every member of the CCN family.

The VIGF polypeptide also has significant similarity to the IBP family. In two adjacent regions, amino acids 51–64 (IBP signature) and 76–90, there is at least 80% identity to the IBP family. These regions are contained within the putative IGF binding domain of the IBPs. The human tissue and cell-type specific expression has been determined by Northern blot analysis. The 2.3–2.4 kb VIGF mRNA is localized in the adult lung and kidney as shown using the procedure of Example 4. VIGF gene expression was undetectable in heart, brain, placenta, liver, skeletal muscle, and pancreas. Cultured human umbilical vein endothelial and aortic smooth muscle cells are cell-types which express VIGF mRNA at a high level while dermal foreskin fibroblasts show a very low level. Together, these results indicate that VIGF is primarily of vascular origin.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–1E (SEQ ID NO:1) or that of the deposited clone or may be a different coding sequence which coding sequence, as a result of the redundancy or degeneracy of the genetic code, encodes the same mature polypeptide as the DNA of FIGS. 1A–1E (SEQ ID NO:1) or the deposited cDNA.

The polynucleotide which encodes for the mature polypeptide of FIGS. 1A–1E (SEQ ID NO:2) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–1E (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–1E (SEQ ID NO:2) or the same mature polypeptide encoded by the cDNA of the deposited clone as well as variants of such polynucleotides which variants encode for a fragment, derivative or analog of the polypeptide of FIGS. 1A–1E (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–1E (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIGS. 1A–1E (SEQ ID NO:1) or the deposited cDNA.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a VIGF polypeptide which has the deduced amino acid sequence of FIGS. 1A–1E (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIGS. 1A–1E (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–1E (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occuring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the VIGF genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila S2 and Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pBSKS, pNH8A, pNH16a, pNH18A, pNH46A (Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The VIGF polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

This VIGF polypeptide of the present invention may be employed in wound-healing and associated therapies concerned with re-growth of tissue, such as connective tissue, skin, bone, cartilage, muscle, lung or kidney.

VIGF polypeptide may also be employed to enhance the growth of vascular smooth muscle and endothelial cells leading to the stimulation of angiogenesis. The VIGF-mediated increase in angiogenesis would be beneficial to ischemic tissues and to collateral coronary development in the heart subsequent to coronary stenosis.

VIGF polypeptide may also be employed during implant fixation to stimulate the growth of cells around the implant and therefore, facilitate its attachment to its intended site.

VIGF polypeptide may also be employed to increase IGF stability in tissues or in serum. It may also increase binding to the IGF receptor. Since IGF has been shown in vitro to enhance human marrow erythroid and granulocytic progenitor cell growth, VIGF polypeptide may also be employed to stimulate erythropoiesis or granulopoiesis.

In accordance with yet a further aspect of the present invention, there is provided a process for utilizing such polypeptides, or polynucleotides encoding such polypeptides, as a research reagent for in vitro purposes related to scientific research, synthesis of DNA and manufacture of DNA vectors, for the purpose of developing therapeutics and diagnostics for the treatment of human disease.

Fragments of the full length VIGF gene may be used as a hybridization probe for a cDNA library to isolate the full length VIGF gene and to isolate other genes which have a high sequence similarity to the VIGF gene or similar biological activity. Probes of this type can be, for example, between 20 and 2000 base pairs. Preferably, however, the probes have between 30 and 50 bases. The probe may also be used to identify a cDNA clone corresponding to a full length transcript and a genomic clone or clones that contain the complete VIGF gene including regulatory and promotor regions, exons, and introns. An example of a screen comprises isolating the coding region of the VIGF gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

This invention provides a method for identification of the receptor for VIGF. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to VIGF, and a cDNA library created from this RNA is divided into pools and used to transfect COS cells or other cells that are not responsive to VIGF. Transfected cells which are grown on glass slides are exposed to labeled VIGF. VIGF can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor.

As an alternative approach for receptor identification, labeled VIGF can be photoaffinity linked with cell membrane or extract preparations that express the receptor molecule. Cross-linked material is resolved by PAGE and exposed to X-ray film. The labeled complex containing the VIGF-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention is also related to a method of screening compounds to identify those which mimic VIGF (agonists) or prevent the effect of VIGF. An example of such a method takes advantage of the ability of VIGF to stimulate the proliferation of endothelial cells in the presence of the comitogen Con A. Human umbilical vein endothelial cells are obtained and cultured in 96-well flat-bottomed culture plates (Costar, Cambridge, Mass.) and supplemented with a reaction mixture appropriate for facilitating proliferation of the cells, the mixture containing Con-A (Calbiochem, La Jolla, Calif.). Con-A and the compound to be screened are added and after incubation at 37° C., cultures are pulsed with $^3$[H]thymidine and harvested onto glass fiber filters (PhD; Cambridge Technology, Watertown, Mass.). Mean $^3$[H]-thymidine incorporation (cpm) of triplicate cultures is determined using a liquid scintillation counter (Beckman Instruments, Irvine, Calif.). Significant $^3$[H]-thymidine incorporation indicates stimulation of endothelial cell proliferation.

To assay for antagonists, the assay described above is performed, however, in this assay VIGF is added along with the compound to be screened and the ability of the compound to inhibit $^3$[H]-thymidine incorporation in the presence of VIGF, indicates that the compound is an antagonist to VIGF. Alternatively, VIGF antagonists may be detected by combining VIGF and a potential antagonist with membrane-bound VIGF receptors or recombinant receptors under appropriate conditions for a competitive inhibition assay. VIGF can be labeled, such as by radioactivity, such that the number of VIGF molecules bound to the receptor can determine the effectiveness of the potential antagonist.

Also, a mammalian cell or membrane preparation expressing the VIGF receptor would be incubated with labeled VIGF in the presence of the compound. The ability of the compound to enhance or block this interaction could then be measured. ALternatively, VIGF, labelled IGF and a potential compound could be incubated under conditions where VIGF would naturally bind to IGF. The extent of this interaction could be measured to determine if the compound is an effective antagonist or agonist.

Examples of potential VIGF antagonists include an antibody, or in some cases, an oligonucleotide, which binds to the polypeptide. Alternatively, a potential antagonist may be a closely related protein, for example, a mutated form of VIGF, which recognizes the VIGF receptor but imparts no effect, thereby competitively inhibiting the action of VIGF.

Another potential VIGF antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251:1360 (1991)), thereby preventing transcription and the production of VIGF. The antisense RNA oligonucleotide hybridizes to the mRNA in vivo and blocks translation of the mRNA molecule into the VIGF (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of VIGF.

Potential VIGF antagonists include small molecules which bind to the active site, the receptor binding site, IGF or other growth factor binding site of the polypeptide thereby blocking the normal biological activity of VIGF. Examples of small molecules include but are not limited to small peptides or peptide-like molecules.

The antagonists may be employed to inhibit tumor neovascularization and the neointimal proliferation of smooth muscle cells prevalent in atherosclerosis and restenosis subsequent to balloon angioplasty.

The antagonists may also be employed to inhibit the over production of scar tissue seen in a keloid which forms after surgery, fibrosis after myocardial infarction, or fibrotic lesions associated with pulmonary fibrosis. The antagonists may be employed in a composition with a pharmaceutically acceptable carrier, e.g., as hereinafter described.

The VIGF polypeptides and antagonist or agonists of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

VIGF in combination with other growth factors including but not limited to, PDGF, IGF, FGF, EGF or TGF-β may accelerate physiological responses as seen in wound healing.

The VIGF polypeptide and agonists and antagonists which are polypeptides, may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

This invention is also related to the use of the VIGF gene as a diagnostic. Detection of a mutated form of VIGF will allow a diagnosis of a disease or a susceptibility to a disease, such as a tumor, since mutations in VIGF may cause tumors.

Individuals carrying mutations in the human VIGF gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding VIGF can be used to identify and analyze VIGF mutations. For example, deletions and insertions can be detected by a change in size of the amplified product in comparison to the normal genotype. Point mutations can be identified by hybridizing amplified DNA to radiolabeled VIGF RNA or alternatively, radiolabeled VIGF antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamidine gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

VIGF protein expression may be linked to vascular disease or neovascularization associated with tumor formation. VIGF has a signal peptide and the mRNA is highly expressed in endothelial cells and to a lesser extent in smooth muscle cells which indicates that the protein is present in serum. Accordingly, an anti-VIGF antibody could be used to diagnose vascular disease or neovascularization associated with tumor formation since an altered level of this polypeptide may be indicative of such disorders.

A competition assay may be employed wherein antibodies specific to VIGF is attached to a solid support and labeled VIGF and a sample derived from the host are passed over the solid support and the amount of label detected attached to the solid support can be correlated to a quantity of VIGF in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, N.Y. (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1
Bacterial Expression and Purification of VIGF

The DNA sequence encoding VIGF, ATCC #75874, was initially amplified using PCR oligonucleotide primers corresponding to the 5' sequences of the processed VIGF protein (minus the signal peptide sequence) and the vector sequences 3' to the VIGF gene. Additional nucleotides corresponding to VIGF were added to the 5' and 3' sequences respectively. The 5' oligonucleotide primer has the sequence 5' CGCAAGCTTA<u>AAT</u>AATTATGCGGTGGACTGC 3' (SEQ ID NO:10) contains a Hind III restriction enzyme site (in bold) followed by 21 nucleotides of VIGF coding sequence starting from the presumed terminal amino acid of the processed protein codon (underlined). The 3' (SEQ ID NO:11) oligonucleotide primer 5' CGCTCTAGA TCAGCGTGGATTTAACCA 3' contains an Xba I restriction site (in bold) followed by the reverse complement of nucleotides corresponding to the carboxy-terminal 5 amino acids and the translational stop codon (underlined). The restriction enzyme sites correspond to the restriction enzyme sites on the bacterial expression vector pQE-9 (Qiagen, Inc. Chatsworth, Calif.). pQE-9 encodes antibiotic resistance (Amp'), a bacterial origin of replication (ori), an IPTG-regulatable promoter operator (P/O), a ribosome binding site (RBS), a 6-His tag and restriction enzyme sites. The VIGF PCR product and pQE-9 were then digested with Hind III and Xba I and ligated together with T4 DNA ligase. The desired recombinants would contain the VIGF coding sequence inserted downstream from the pQE-9 encoded histidine tag and the ribosome binding site. The ligation mixture was then used to transform E. coli strain M15 [pREP4] (Qiagen, Inc.) by the procedure described in Sambrook, J. et al., Molecular Cloning: A Laboratory Manual, Cold Spring Laboratory Press, (1989). M15 [pREP4] contains multiple copies of the plasmid pREP4, which expresses the laci repressor and also confers kanamycin resistance (Kan'). Transformants were identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 μg/ml) and Kan (25 μg/ml). The O/N culture was used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours such that there is an exponential growth culture present. Cells were then harvested by centrifugation. The VIGF/6-Histidine-containing M15[pREP4] cells were lysed in 6M GnHCl,50 mM NaPO$_4$ at pH 8.0. The lysate was loaded on a Nickel-Chelate column and the flow-through collected. The column was washed with 6M GnHCl, 50 mM NaPO$_4$ at pH 8.0, 6.0 and 5.0. The VIGF fusion protein (>90% pure) was eluted at pH 2.0. Samples from the pre-column lysate (FIG. 3, lane 2), column flow through (lane 3), pH 5.0 wash (lane 4), and pH 2.0 eluate (lane 5) were precipitated with sodium deoxycholate and trichloroacetic acid. For the purpose of renaturation, the pH 2.0 eluate was adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate. To run the gel, the pellets were resuspended in SDS/NaOH and SDS-PAGE loading buffer, heat denatured, then electrophoresed on a 15% denaturing polyacrylamide gel. The Gibco BRL low range molecular weight standard was also electrophoresed (lane 1). The proteins were visualized with Coomassie Brilliant Blue R-250 stain. FIG. 3 shows an SDS-polyacrylamide gel which displays the results of VIGF purification.

EXAMPLE 2

Cloning and Expression of VIGF Using the Baculovirus Expression System

The DNA sequence encoding the full length VIGF protein, ATCC #75874, is digested with the restriction enzymes PvuII and XbaI. The 639 nucleotide PvuII, XbaI fragment contains the entire VIGF coding region plus 11 and 77 nucleotides of 5' and 3' untranslated DNA, respectively. This fragment, designated F2, is isolated from a 1% agarose gel using a commercially available kit ("Geneclean", BIO 101 Inc., La Jolla, Calif.).

The vector pA2 is used for the expression of the VIGF protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhidrosis virus (AcMNPV) followed by the recognition sites for the restriction endonucleases SmaI and XbaI. The polyadenylation site of the simian virus (SV)40 is used for efficient polyadenylation. For an easy selection of recombinant viruses the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pA2 such as, pRG1, pAc373, pVL941 and pAcIM1 (Luckow, V. A. and Summers, M. D., Virology, 170:31–39).

The plasmid is digested with the restriction enzymes SmaI and XbaI and then dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. E. coli strain XL1 Blue (Stratagene Cloning Systems, 11011 North Torrey Pines Road La Jolla, Calif. 92037) are then transformed and bacteria identified that contained the plasmid (pBac VIGF) with the VIGF cDNA using the enzymes BamHI and XbaI. The sequence of the cloned fragment is confirmed by DNA sequencing.

5 μg of the plasmid pBac VIGF is cotransfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmid pBac VIGF are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added dropwise to the Sf9 insect cells (ATCC CRL 1711) seeded in a 35 mm tissue culture plate with 1 ml Grace' medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells and blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculoviruses is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-VIGF at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) are added. The cells are further incubated for 16 hours before they are harvested by centrifugation and the labelled proteins visualized by SDS-PAGE and autoradiography.

EXAMPLE 3

Expression of Recombinant VIGF in CHO Cells

The vector pN346 is used for the expression of the VIGF protein. Plasmid pN346 is a derivative of the plasmid pSV2-dhfr [ATCC Accession No. 37146]. Both plasmids contain the mouse dhfr gene under control of the SV40 early promoter. Chinese hamster ovary or other cells lacking dihydrofolate activity that are transfected with these plasmids can be selected by growing the cells in a selective medium (alpha minus MEM, Lift Technologies) supplemented with the chemotherapeutic agent methotrexate. The amplication of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the dhfr gene it is usually co-amplified and overexpressed. Subsequently, when the methotrexate is withdrawn, cell lines contain the amplified gene integrated into the chromosome(s).

Plasmid pN346 contains for the expression of the gene of interest a strong promoter of the long terminal repeat (LTR) of the Rouse Sarcoma Virus (Cullen, et al., Molecular and Cellular Biology, March 1985, 438–447) plus a fragment isolated from the enhancer of the immediate early gene of human cytomegalovirus (CMV) (Boshart et al., Cell 41:521–530, 1985). Downstream of the promoter are the following single restriction enzyme cleavage sites that allow the integration of the genes: BamHI, Pvull, and Nrul. Behind these cloning sites the plasmid contains translational stop codons in all three reading frames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosome can also be selected upon co-transfection with a selectable marker such as gpt, G418 or hygromycin. It is advantageous to use more than one selectable marker in the beginning, e.g. G418 plus methotrexate.

The plasmid pN346 is digested with the restriction enzyme BamHI and then dephosphorylated using calf intestinal phosphatase by procedures known in the art. The vector is then isolated from a 1% agarose gel.

The DNA sequence encoding the full length VIGF protein, ATCC #75874, is amplified using PCR oligonucleotide primers corresponding to the 5' and 3' sequences of the gene:

The 5' primer has the sequence 5' CGCAGATCTCCGC-CACCATGAAGAGCGTCTTGCTGCTG 3' (SEQ ID NO:12) and contains a BglII restriction enzyme site (in bold) followed by 8 nucleotides resembling an efficient signal for the initiation of translation in eukaryotic cells (Kozak, M., J. Mol. Biol., 196:947–950, (1987)). The remaining nucleotides correspond to the amino terminal 7 amino acids including the translational initiation codon (underlined). The 3' primer has the sequence 5' CGCAGATCTAGCCT-TCTCTCAGAAATCACA 3' (SEQ ID NO:13) and contains a BglII restriction site (in bold) and 21 nucleotides that are the reverse complement of 3' untranslated DNA starting 7 nucleotides downstream from the translational stop codon. The PCR product is digested with BglII and purified on a 1% agarose gel using a commercially available kit ("Geneclean," BIO 101 Inc., La Jolla, Calif.). This fragment is then ligated to BamHI digested, phosphatased pN346 plasmid with T4 DNA ligase. Xl1Blue (Stratagene) *E. coli* are transformed and plated on LB, 50 μg/ml ampicillin plates. Colonies bearing the desired recombinant in the proper orientation are screened for by PCR with a 5' primer which corresponds to the Rous sarcoma virus promoter and a 3' primer which corresponds to the reverse complement of VIGF codons 73–79. The sequence of the cloned fragment is confirmed by DNA sequencing.

Transfection of CHO-dhfr-Cells

Chinese hamster ovary cells lacking an active DHFR enzyme are used for transfection. 5 μg of the expression plasmid pN346VIGF are cotransfected with 0.5 μg of the plasmid pSVneo using the lipofectin method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10–14 days. After this period, single clones are trypsinized and then seeded in 6-well petri dishes using different concentrations of methotrexate (25, 50 nm, 100 nm, 200 nm, 400 nm). Clones growing at the highest concentrations of methotrexate are then transferred to new 6-well plates containing even higher concentrations of methotrexate (500 nM, 1 μM, 2 μM, 5 μM). The same procedure is repeated until clones grew at a concentration of 100 μm.

The expression of the desired gene product is analyzed by Western blot analysis and SDS-PAGE.

EXAMPLE 4

Tissue Localization of VIGF Gene Expression by Northern Blot Analysis

A multiple tissue Northern blot (Clontech Laboratories, Inc., 4030 Fabian Way; Palo Alto, Calif. 94303) containing 2 ug of human adult brain, heart, placenta, lung, liver skeletal muscle, kidney, and pancreas poly A+ mRNA per lane is prehybridized in Church buffer (Church, G. M. & Gilbert, W., Proc. Natl. Acad. Sci. USA 81, 1991–1995 (1984)) at 60° C. for one hour. The DNA sequence coding for VIGF, ATCC# 75874, is amplified from the full length cDNA cloned in pBluescript SK(-) using the M13 Forward (5' GGGTTTTCCCAGTCACGAC 3') (SEQ ID NO:14) and Reverse (5' ATGCTTCCGGCTCGTATG 3') (SEQ ID NO:15) primers. Twenty-five nanograms of PCR product is random primer radiolabeled (Prime-It II, Stratagene Cloning Systems, 11011 North Torrey Pines Rd.; La Jolla, Calif. 92037) with $^{32}$P-dCTP. The heat denatured VIGF probe is added directly to the prehybridization buffer and incubated 16 hr at 60° C. Two ten minute washes are performed in 0.2×SSC, 0.1% SDS at 60° C. Autoradiography is performed at -80° C.

Figure 4:
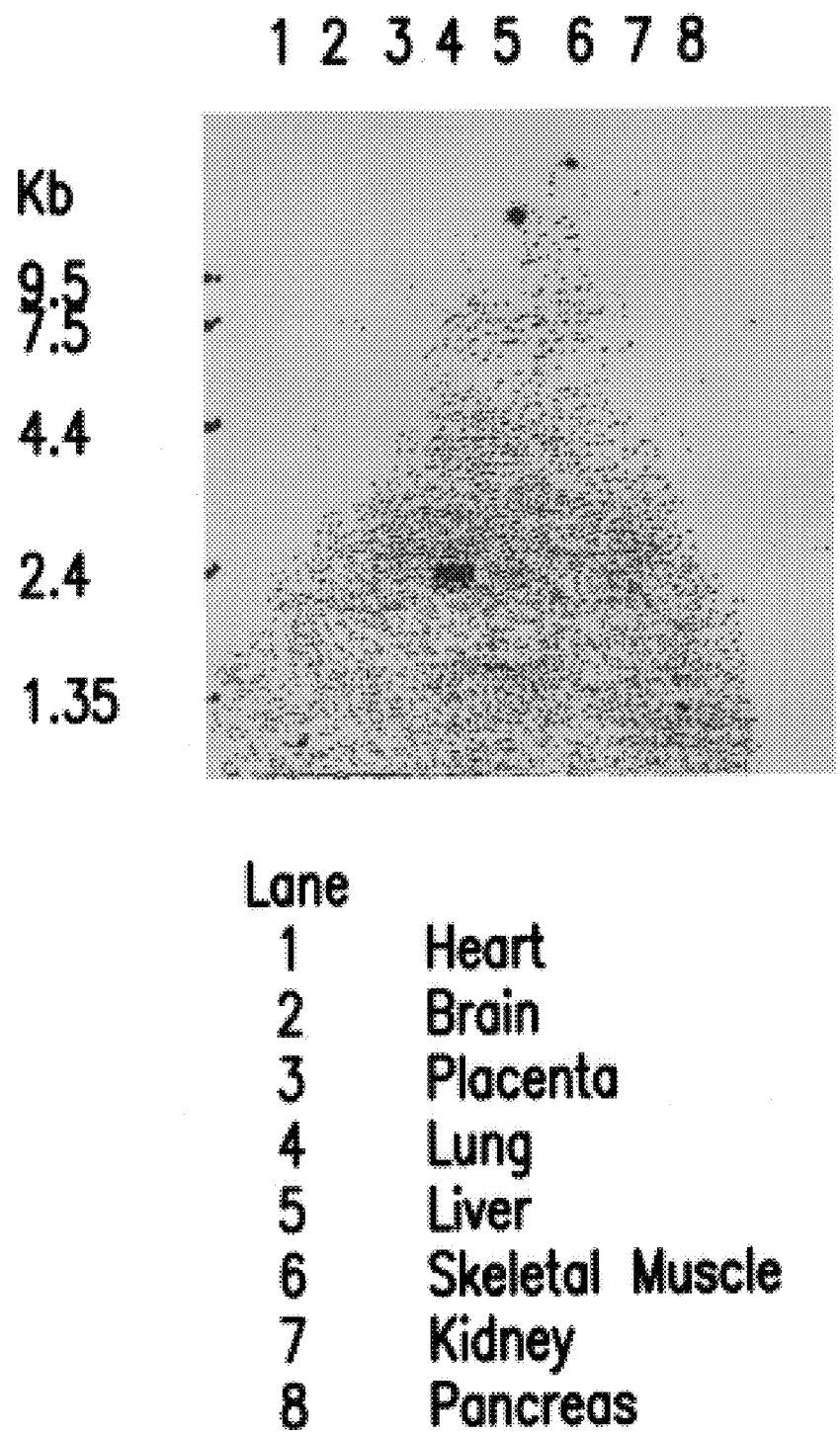
FIG. 4 shows a gel which displays the results of a Northern Blot analysis performed on VIGF.

A 2.3 kb transcript is seen in lung and kidney after a four day exposure (FIG. 4).

EXAMPLE 5

Cell-Type Analysis of VIGF Gene Expression by Northern Blot Analysis

Human umbilical vein endothelial, aortic smooth muscle, dermal foreskin fibroblast cells (Clonetics, 9620 Chesapeake Drive, Suite #201; San Diego, Calif. 92123) were grown to 75–90% confluency. Total RNA is extracted with RNAzol (Biotecx Laboratories, Inc., 6023 South Loop East Houston, Tex. 77033). A 1.2% agarose formaldehyde gel is prepared and run with 20 ug of total RNA per lane and an RNA ladder size marker (Life Technologies, Inc., 8400 Helgerman Ct., P.O. Box 6009 Gaithersburg, Md. 20884) according to Sambrook et al. (1989). The RNA is transferred overnight to Hybond N+ (Amersham Corp., 2636 South Clearbrook Drive; Arlington Heights, Ill. 60005) and bound to the membrane with a Stratalinker UV Crosslinker (Stratagene Cloning Systems, La Jolla, Calif.). The blot is prehybridized in Church buffer (Church, G. M. & Gilbert, W., PNAS, USA 81:1991–1995 (1984)) at 60° C. for one hour. The DNA sequence encoding VIGF, ATCC # 75874, is amplified from the full length cDNA cloned in pBluescript SK(−) using the M13 Forward (5' GGGTTTTCCCAGTCACGAC 3') (SEQ ID NO:16) and Reverse (5' ATGCTTCCGGCTCGTATG 3') (SEQ ID NO:17) primers. Twenty-five nanograms of PCR product is random primer radiolabeled (Prime-It II, Stratagene) with $^{32}$P-dCTP. The heat denatured VIGF probe is added directly to the prehybridization buffer and incubated 16 hr at 60° C. Two ten minute washes were performed in 0.2×SSC, 0.1% SDS at 60° C. Autoradiography is performed at −80° C. A 2.3–2.4 kb transcript is seen in umbilical vein endothelial (lane 1) and aortic smooth muscle cells (lane 2) after a two hour exposure (FIG. 5A) and also in dermal foreskin fibroblast (lane 3) cells after a 36 hour exposure (FIG. 5B).

Numerous modifications and variations of the present invention are possible in light of the above teachings and, therefore, within the scope of the appended claims, the invention may be practiced otherwise than as particularly described.

What is claimed is:

1. An isolated polypeptide comprising an amino acid sequence selected from the group consisting of:
   (a) a mature portion of the protein as set forth in SEQ ID NO:2;
   (b) amino acids +1 to +184 of SEQ ID NO:2;
   (c) amino acids +2 to +184 of SEQ ID NO:2;
   (d) a mature portion of the protein encoded by the cDNA contained in ATCC Deposit No.75874;
   (e) a proprotein portion of a protein encoded by the cDNA contained in ATCC Deposit No.75874; and
   (f) the amino acid sequence encoded by the cDNA contained in ATCC Deposit No.75874.

2. The isolated polypeptide of claim 1, wherein said amino acid sequence is (a).

3. The isolated polypeptide of claim 2, wherein said amino acid sequence comprises amino acids +22 to +184 of SEQ ID NO:2.

4. The isolated polypeptide of claim 3 further comprising a heterologous polypeptide.

5. The isolated polypeptide of claim 2 further comprising a heterologous polypeptide.

6. The isolated polypeptide of claim 1, wherein said amino acid sequence is (b).

7. The isolated polypeptide of claim 6 further comprising a heterologous polypeptide.

8. The isolated polypeptide of claim 1, wherein said amino acid sequence is (c).

9. The isolated polypeptide of claim 8 further comprising a heterologous polypeptide.

10. The isolated polypeptide of claim 1, wherein said amino acid sequence is (d).

11. The isolated polypeptide of claim 10 further comprising a heterologous polypeptide.

12. The isolated polypeptide of claim 1, wherein said amino acid sequence is (e).

13. The isolated polypeptide of claim 12 further comprising a heterologous polypeptide.

14. The isolated polypeptide of claim 1, wherein said amino acid sequence is (f).

15. The isolated polypeptide of claim 14 further comprising a heterologous polypeptide.

16. A composition comprising the polypeptide of claim 1.

17. An isolated polypeptide comprising an amino acid sequence selected from the group consisting of:
   (a) a protein fragment of the amino acid sequence of SEQ ID NO:2, wherein said fragment has endothelial cell proliferative activity; and
   (b) a protein fragment encoded by the human cDNA contained in ATCC Deposit No. 75874, wherein said fragment has endothelial cell proliferative activity.

18. The isolated polypeptide of claim 17, wherein said amino acid sequence is (a).

19. The isolated polypeptide of claim 18 further comprising a heterologous polypeptide.

20. The isolated polypeptide of claim 17, wherein said amino acid sequence is (b).

21. The isolated polypeptide of claim 20 further comprising a heterologous polypeptide.

22. A composition comprising the polypeptide of claim 17.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH: 1271 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
CTGCTTCCCA CCAGCAAAGA CCACGACTGG AGAGCCGAGC CGGAGCAGCT GGGAAACATG     60

AAGAGCGTCT TGCTGCTGAC CACGCTCCTC GTGCCTGCAC ACCTGGTGGC CGCCTGGAGC    120

AATAATTATG CGGTGGACTG CCCTCAACAC TGTGACAGCA GTGAGTGCAA AAGCAGCCCG    180

CGCTGCAAGA GGACAGTGCT CGACGACTGT GGCTGCTGCC GAGTGTGCGC TGCAGGGCGG    240

GGAGAAACTT GCTACCGCAC AGTCTCAGGC ATGGATGGCA TGAAGTGTGG CCCGGGGCTG    300

AGGTGTCAGC CTTCTAATGG GGAGGATCCT TTTGGTGAAG AGTTTGGTAT CTGCAAAGAC    360

TGTCCCTACG GCACCTTCGG GATGGATTGC AGAGAGACCT GCAACTGCCA GTCAGGCATC    420

TGTGACAGGG GGACGGGAAA ATGCCTGAAA TTCCCCTTCT TCCAATATTC AGTAACCAAG    480

TCTTCCAACA GATTTGTTTC TCTCACGGAG CATGACATGG CATCTGGAGA TGGCAATATT    540

GTGAGAGAAG AAGTTGTGAA AGAGAATGCT GCCGGGTCTC CCGTAATGAG GAAATGGTTA    600

AATCCACGCT GATCCCGGCT GTGATTTCTG AGAGAAGGCT CTATTTTCGT GAYTGTTCAA    660

CACACAGCCA ACATTTTAGG AACTTTCTAG ATTATAGCAT AAGGACATGT AATTTTTGAA    720

GACCAAATGT GATGCATGGT GGATCCAGAA AACAAAAAGT AGGATACTTA CAATCCATAA    780

CATCCATATG ACTGAACACT TGTATGTGTT TGTTAAATAT TCGAATGCAT GTAGATTTGT    840

TAAATGTGTG TGTATAGTAA CACTGAAGAA CTAAAAATGC AATTTAGGTA ATCTTACATG    900

GAGACAGGTC AACCAAAGAG GGAGCTAGGC AAAGCTGAAG ACCGCAGTGA GTCAAATTAG    960

TTCTTTGACT TTGATGTACA TTAATGTTGG GATATGGAAT GAAGACTTAA GAGCAGGAGA   1020

AGATGGGGAG GGGGTGGGAG TGGGAAATAA AATATTTAGC CCTTCCTTGG TAGGTAGCTT   1080

CTCTAGAATT TAATTRTGCT TTTTTTTTTT TTTTTGGGCT TTGGGAAAAG TCAAAATAAA   1140

ACAACCAGAA AACCCCTGAA GGAAGTAAGA TGTTTGAAGC TTATGGAAAT TTGAGTAACA   1200

AACAGCTTTG ANCTGAGAGC AATTYCAAAA GGCTGCTGAT GTAGCCCCCG GGTTNCCTNT   1260

NTCTNAAGGA C                                                       1271
```

(2) INFORMATION FOR SEQ ID NO:2:

(i) SEQUENCE CHARACTERISTICS:
        (A) LENGTH: 184 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Lys Ser Val Leu Leu Leu Thr Thr Leu Leu Val Pro Ala His Leu
 1               5                  10                  15

Val Ala Ala Trp Ser Asn Asn Tyr Ala Val Asp Cys Pro Gln His Cys
            20                  25                  30

Asp Ser Ser Glu Cys Lys Ser Ser Pro Arg Cys Lys Arg Thr Val Leu
        35                  40                  45

Asp Asp Cys Gly Cys Cys Arg Val Cys Ala Ala Gly Arg Gly Glu Thr
50                  55                  60

Cys Tyr Arg Thr Val Ser Gly Met Asp Gly Met Lys Cys Gly Pro Gly
65                  70                  75                  80

Leu Arg Cys Gln Pro Ser Asn Gly Glu Asp Pro Phe Gly Glu Glu Phe
            85                  90                  95

Gly Ile Cys Lys Asp Cys Pro Tyr Gly Thr Phe Gly Met Asp Cys Arg
            100                 105                 110

Glu Thr Cys Asn Cys Gln Ser Gly Ile Cys Asp Arg Gly Thr Gly Lys
            115                 120                 125

Cys Leu Lys Phe Pro Phe Phe Gln Tyr Ser Val Thr Lys Ser Ser Asn
130                 135                 140

Arg Phe Val Ser Leu Thr Glu His Asp Met Ala Ser Gly Asp Gly Asn
145                 150                 155                 160

Ile Val Arg Glu Glu Val Val Lys Glu Asn Ala Ala Gly Ser Pro Val
            165                 170                 175

Met Arg Lys Trp Leu Asn Pro Arg
            180
```

(2) INFORMATION FOR SEQ ID NO:3:

(i) SEQUENCE CHARACTERISTICS:
        (A) LENGTH: 90 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Gly Ser Ala Gly Ala Arg Pro Ala Leu Ala Ala Leu Leu Cys
 1               5                  10                  15

Leu Ala Arg Leu Ala Leu Gly Ser Pro Cys Pro Ala Val Cys Gln Cys
            20                  25                  30

Pro Ala Ala Ala Pro Gln Cys Ala Pro Gly Val Gly Leu Val Pro Asp
        35                  40                  45

Gly Cys Gly Cys Cys Lys Val Cys Ala Lys Gln Leu Asn Glu Asp Cys
50                  55                  60

Ser Arg Thr Gln Pro Cys Asp His Thr Lys Gly Leu Glu Cys Asn Arg
65                  70                  75                  80

Leu Val Asn Asp Ile His Lys Phe Arg Asp
            85                  90
```

(2) INFORMATION FOR SEQ ID NO:4:

(i) SEQUENCE CHARACTERISTICS:
        (A) LENGTH: 90 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Ser Ser Ser Thr Phe Arg Thr Leu Ala Val Ala Val Thr Leu Ala
1               5                   10                  15

His Leu Thr Arg Leu Ala Leu Ser Thr Cys Pro Ala Ala Cys His Cys
            20                  25                  30

Pro Leu Glu Ala Pro Lys Cys Ala Pro Gly Val Gly Leu Val Arg Asp
        35                  40                  45

Gly Cys Gly Cys Lys Val Cys Ala Lys Gln Leu Asn Glu Asp Cys
    50                  55                  60

Ser Lys Thr Gln Pro Cys Asp His Thr Lys Gly Leu Glu Cys Asn Ser
65              70                  75                  80

Leu Phe Asn Asp Ile His Lys Phe Arg Asp
                85                  90
```

(2) INFORMATION FOR SEQ ID NO:5:

(i) SEQUENCE CHARACTERISTICS:
        (A) LENGTH: 93 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65              70                  75                  80

Phe Cys Asp Tyr Tyr Arg Lys Met Tyr Gly Asp Met Ala
                85                  90
```

(2) INFORMATION FOR SEQ ID NO:6:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Leu Ala Ser Val Ala Gly Pro Ile Ser Leu Ala Leu Val Leu Leu
1               5                   10                  15

Ala Leu Cys Thr Arg Thr Ala Thr Gly Gln Asp Cys Ser Ala Gln Cys
            20                  25                  30
```

```
Gln Cys Ala Ala Glu Ala Ala Pro His Tyr Tyr Arg Lys Met Tyr Gly
        35                  40                  45

Asp Met Ala
    50
```

(2) INFORMATION FOR SEQ ID NO:7:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Met Glu Thr Gly Gly Gly Gln Gly Leu Pro Val Leu Leu Leu Leu Leu
1               5                  10                  15

Leu Leu Leu Arg Pro Cys Glu Val Ser Gly Arg Glu Ala Ala Cys Pro
        20                  25                  30

Arg Pro Cys Gly Gly Arg Cys Pro Ala Glu Pro Pro Arg Asp Pro Met
        35                  40                  45

Ser Ser Glu Ala Lys Ile
    50
```

(2) INFORMATION FOR SEQ ID NO:8:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Met Gln Arg Ala Arg Pro Thr Leu Trp Ala Ala Ala Leu Thr Leu Leu
1               5                  10                  15

Val Leu Leu Arg Gly Pro Pro Val Ala Arg Ala Gly Ala Ser Ser Gly
        20                  25                  30

Gly Leu Gly Pro Val Val Arg Cys Glu Pro Cys Val Ala Arg Ala Leu
        35                  40                  45

Ala Arg
    50
```

(2) INFORMATION FOR SEQ ID NO:9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GCGCCNNCAN NNNNNC                                        16

(2) INFORMATION FOR SEQ ID NO:10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CGCAAGCTTA AATAATTATG CGGTGGACTG C                                                      31

(2) INFORMATION FOR SEQ ID NO:11:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:11:

CGCTCTAGAT CAGCGTGGAT TTAACCA                                                           27

(2) INFORMATION FOR SEQ ID NO:12:

(i) SEQUENCE CHARACTERISTICS:
          (A) LENGTH: 38 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:12:

CGCAGATCTC CGCCACCATG AAGAGCGTCT TGCTGCTG                                               38

(2) INFORMATION FOR SEQ ID NO:13:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:13:

CGCAGATCTA GCCTTCTCTC AGAAATCACA                                                        30

(2) INFORMATION FOR SEQ ID NO:14:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:14:

GGGTTTTCCC AGTCACGAC                                                                    19

(2) INFORMATION FOR SEQ ID NO:15:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:15:

ATGCTTCCGG CTCGTATG                                                                     18

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GGGTTTTCCC AGTCACGAC                                        19

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

ATGCTTCCGG CTCGTATG                                         18